(12) United States Patent
Samain

(10) Patent No.: US 9,138,041 B2
(45) Date of Patent: Sep. 22, 2015

(54) SYSTEM COMPRISING AN ELECTRONIC MEANS EXECUTING A PROGRAM AND CONTROLLING AN ADJUSTMENT SYSTEM

(75) Inventor: Henri Samain, Bievres (FR)

(73) Assignee: L'OREAL, Paris (FR)

( * ) Notice: Subject to any disclaimer, the term of this patent is extended or adjusted under 35 U.S.C. 154(b) by 386 days.

(21) Appl. No.: 13/574,829

(22) PCT Filed: Feb. 2, 2011

(86) PCT No.: PCT/IB2011/050445
§ 371 (c)(1),
(2), (4) Date: Oct. 5, 2012

(87) PCT Pub. No.: WO2011/095933
PCT Pub. Date: Aug. 11, 2011

(65) Prior Publication Data
US 2013/0037043 A1    Feb. 14, 2013

Related U.S. Application Data

(60) Provisional application No. 61/317,063, filed on Mar. 24, 2010.

(30) Foreign Application Priority Data

Feb. 3, 2010   (FR) ..................................... 10 50756

(51) Int. Cl.
*G06F 17/00*     (2006.01)
*A45D 44/00*     (2006.01)
*G06F 19/00*     (2011.01)

(52) U.S. Cl.
CPC .......... *A45D 44/005* (2013.01); *G06F 19/3462* (2013.01)

(58) Field of Classification Search
CPC .. G06F 19/3462; A45D 44/005; A45D 34/04; B01F 13/1055
See application file for complete search history.

(56) References Cited

U.S. PATENT DOCUMENTS 5,785,960 A  *  7/1998  Rigg et al. ...................... 424/63
5,812,064 A  *  9/1998  Barbour ...................... 340/5.91
(Continued)

FOREIGN PATENT DOCUMENTS

FR     2 807 346 A1   10/2001
FR     2 931 940 A1   12/2009
(Continued)

OTHER PUBLICATIONS

International Search Report issued in International Patent Application No. PCT/IB2011/050445 dated Apr. 7, 2011.
(Continued)

*Primary Examiner* — Timothy Waggoner
(74) *Attorney, Agent, or Firm* — Oliff PLC

(57) ABSTRACT

A cosmetic or dermatological system includes a packaging and dispensing device including one or more compositions on the basis of which a product is delivered, an adjustment system coupled or able to be coupled to the packaging and dispensing device, making it possible to modify the amount dispensed and/or at least one property of the product dispensed by the packaging and dispensing device, an electronic means for executing a program and acting automatically on the adjustment system, or for indicating to the user an action to be exerted on the adjustment system, to make the adjustment evolve in the course of the use of the device, the program determining the evolution of the adjustment as a function at least of a quantity representative of the number of uses of said device or of the amount of said product or of at least one of said compositions and already dispensed.

8 Claims, 4 Drawing Sheets

(56) References Cited

U.S. PATENT DOCUMENTS

Figure 1:
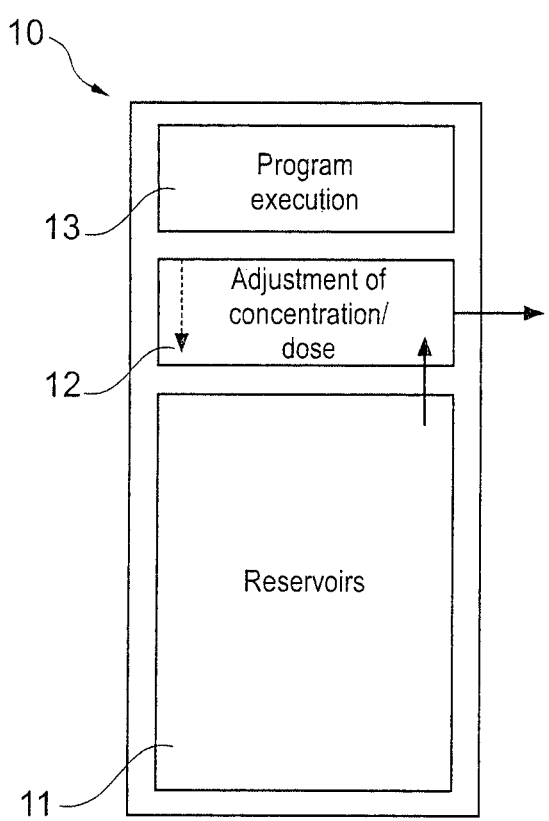

| | | |
|---|---|---|
| 6,986,442 B2 * | 1/2006 | Engel et al. .................... 222/63 |
| 8,224,481 B2 * | 7/2012 | Bylsma et al. ................ 700/239 |
| 2006/0108247 A1 * | 5/2006 | Liechty et al. ................ 206/385 |
| 2011/0288680 A1 | 11/2011 | Samain et al. |

FOREIGN PATENT DOCUMENTS

| | | |
|---|---|---|
| FR | 2 937 511 A1 | 4/2010 |
| JP | A-2008-237718 | 10/2008 |
| WO | WO 98/30189 A2 | 7/1998 |
| WO | WO 02/094423 A1 | 11/2002 |
| WO | WO 2008/068337 A1 | 6/2008 |
| WO | WO 2010/046883 A1 | 4/2010 |

OTHER PUBLICATIONS

Written Opinion of the International Searching Authority issued in International Patent Application No. PCT/IB2011/050445 dated Apr. 7, 2011.

* cited by examiner

SYSTEM COMPRISING AN ELECTRONIC MEANS EXECUTING A PROGRAM AND CONTROLLING AN ADJUSTMENT SYSTEM

The present invention relates to the packaging and dispensing of cosmetic or dermatological products, especially but not exclusively of products in a fluid form, suitable for application to the skin, mucous membranes or keratinic fibres.

The invention relates more particularly to care treatments of the skin, armpits, scalp, nails and lips and treatments modifying the look, colour and form of the hair, lips or skin.

BACKGROUND

A need exists to be able to tailor cosmetic products into numerous versions, so as to be able to accommodate various situations.

Manufacturers have invested a great deal in order to be able to cope with the diversity of cases, by producing the largest number of possible versions. Although they offer numerous variants, it often happens that this solution is not satisfactory.

For example, taking the case of a person treating their skin, the latter can:
 either apply one and the same product throughout the duration of a treatment,
 or apply several products corresponding to the prescription required by their skin in the course of the treatment.

The first approach, though it does not give optimum results, presents the advantage of being simple.

The second approach may give better results but is complex and expensive. Moreover, the person must find the instructions corresponding to their case, and know how to translate them into a mode of application. This approach also presents the drawback of requiring high concentration from the user so as not to confuse the various products used during treatment.

Hitherto there does not exist any system making it possible to optimize a cosmetic treatment, in a simple manner. For this reason, in general, users must content themselves with the first approach and employ just a single product. This may give rise to mistakes of overdosage or under-dosage.

The same holds in respect of protection from the sun. Indeed, it is known that the dosage of photoprotection active agents may evolve over time as the skin tans and becomes protected by tanning. A significant dosage is required during the first few days of exposure. Conversely, the dosage may be reduced after a few days. It is difficult to optimize the strength of the photoprotection product. It follows that users sometimes try to optimize the application of the product themselves. For this purpose, people generally use their sunscreen protection product at the start of holidays and then abandon it after a few days. This "intuitive" optimization approach often gives undesirable results.

The same holds in respect of care products for the scalp, where some users are seen to sometimes hesitate between continuing a treatment and stopping it.

Moreover, a difficulty related to certain treatments resides in the fact that these treatments do not give visible effects during application or immediately after application. Thus, the user cannot be guided by the immediate results in order to decide whether or not to continue the treatment, and still less whether the use should modify the dosage. The user sometimes follows a general prescription which is not necessarily tailored to their case. The treatments concerned are for example treatments for strengthening the nails, the armpits against perspiration, the lips and the skin to combat dryness, hair which is too greasy or too dry.

It is also possible to cite treatments affording a durable colour, for example for dyeing the hair or skin. In these cases, the user, seeing the result, is more comfortable with optimizing the use of the products during subsequent applications. However, in so far as it is difficult to evaluate the evolution of the colour over time, it is also difficult to identify the best application procedures for maintaining it over time.

Finally, the user is often faced with a problem of choice when confronted with several versions. They may hesitate to choose one strength rather than another. They may purchase several versions but this solution is not practical, if only in regard to the clutter and cost imposed by this solution.

Moreover, although manufacturers try to clearly identify the potency level of their products, and display corresponding information on the packaging, the user may make a mistake at the time of application. The business of identifying the brands requires the use of colours or logos on the packaging, serving as recognition signs for consumers. If the manufacturers add other signs so that the users can recognize the potency level, these additional signs may be difficult to recognize or to memorize.

The requirement to provide for various strength levels relates for example to products for protection against the sun, drying, heat or cold, antiperspirant and deodorant products, fragrances and hair gels.

The products can be made with several strength levels or made with a single potency level and rely on the user to dose the application of the product so as to adjust its strength.

For example, antiperspirants can be produced in several versions. However, most of the time, manufacturers do not opt for this approach since studies show that users do not wish to burden themselves with the clutter of several products. The user can adjust the potency of their product by altering the amount applied. However, this poses problems since it is difficult to apply small amounts. It is fairly easy to apply large amounts but the user may then be bothered by the problems of discomfort that this generates, for example as regards the moist feel and look persisting for a number of minutes after application.

Moreover, certain products may not be the subject of versions in several potency levels. This is typically the case for products which already exist in multi-coloured form, such as hair dyeing products for example.

Producing versions of these dyeing products in different potency levels would unacceptably multiply the number of products to be offered. In these cases, the user has no solution for adapting their product as a function of the time of use, and is often far removed from an optimized result.

Patent application FR 2 807 346 describes a flask comprising an electronic circuit making it possible to deliver a message when the user presses a product delivery button. The flask may comprise at least one sensor of an exterior physical parameter, in particular a sensor of ambient luminosity and/or of ambient temperature. The electronic circuit may comprise a microcontroller receiving data from a clock. The message delivered may take account of the time or the period elapsed since the last use.

Patent application WO 98/30189 describes a packaging device making it possible to modify a cosmetic composition as a function of a physical quantity of the ambient environment, measured by a sensor.

SUMMARY

There exists a need to further refine systems for delivering a cosmetic or dermatological product, so as to remedy all or some of the problems set forth hereinabove.

The invention aims to meet this requirement and its subject is, according to one of the aspects thereof, a cosmetic or dermatological system comprising:

- a packaging and dispensing device comprising one or more compositions on the basis of which a product is delivered,
- an adjustment system coupled or able to be coupled to the packaging and dispensing device, making it possible to modify the amount dispensed and/or at least one property of the product dispensed by the packaging and dispensing device,
- an electronic means for executing a program and acting automatically on the adjustment system, or for indicating to the user an action to be exerted on the adjustment system, so as to make the adjustment evolve in the course of the use of the device.

The electronic means may comprise any kind of processor and/or controller. Various hardware may be used such as personal computers, programmable electronic boards (comprising analog circuits and/or integrated circuits), personal digital assistants, mobile telephones, tablets, pcs, etc.

The program can advise the system as to the adjustment to be performed as a function at least of a quantity representative of the number of uses of said device and/or of the amount of product already dispensed and/or of the amount of at least one of said starting compositions already dispensed.

A further subject of the invention, according to another of the aspects thereof, is a cosmetic or dermatological system, comprising:

- a packaging and dispensing device comprising one or more compositions on the basis of which a product is delivered,
- an adjustment system coupled or able to be coupled to the packaging and dispensing device, making it possible to modify the amount dispensed and/or at least one property of the product dispensed by the packaging and dispensing device,
- an electronic means for executing a program containing a predefined law of evolution of the adjustment in the course of successive uses and for acting automatically on the adjustment system, or for indicating to the user an action to be exerted on the adjustment system, so as to comply with said law of evolution.

The adjustment resulting from the execution of the program can also, for example, be independent of the evolution of the climatic environment of the system, independent of the date or of a duration of use or elapsed between the uses of the system, and/or independent of the reception of data transmitted by a data transmitter external to the system.

Said aforementioned quantity may be chosen from among the number of uses of the device, the level of at least one composition in a corresponding reservoir, and the amount of product dispensed. Thus, in exemplary implementations of the invention, the system can monitor the level of at least one reservoir, measure the amount of product dispensed and/or count the uses. The number of uses corresponds for example to the number of times that one or more doses of product are dispensed, the uses being for example separated by a relatively large time interval, for example greater than an hour. The number of uses can further correspond, more simply, to the number of times that a dispensing mechanism is actuated, this mechanism possibly for example being reduced to a flexible wall of a receptacle, the user pressing this wall to dispense the product. The number of uses may further correspond to the number of times that a closure or protection member is actuated or displaced so as to permit the dispensing of the product or to the number of times that the device is lifted up and for example inverted in order to dispense product under gravity. The number of uses may also be incremented by a specific action of the user on a button or other member on which the user can act.

Several parameters may be taken into account by the system, as appropriate, in order to distinguish a manipulation without product dispensing and a manipulation of the device with product dispensing.

For example, the device can be devised to measure its weight so as to detect that a product dispensing has taken place. The weighing may be done for example according to the teaching of patent application FR 2 931 940.

The reservoir may for example have a cross section of greater than 1 cm2.

The product delivered may be applied as is, with no step of prior dilution.

The products dispensed by virtue of a system according to the invention may be cosmetic products or products having a physiological activity.

The invention applies to colour products such as makeup products, for example foundations, powders, eyeliners, mascaras, lipsticks, glosses, nail varnishes, blushers, etc. and to hair products, for example oxidation dyes, direct dyes, etc.

The content of active agents, for example dyeing agents, for example pigments, waxes, powders, sheen agents, retention agents, may be adjusted as a function of the execution of the program, for example as a function of the number of uses since an initialization of the system. For example, the contents of dyes, for example bases and couplers, direct dyes, DHA, etc., and of pigments may be adjusted in nature, in amount and in ratio so as to match the treatment, for example by complying with a predefined law for the evolution of the adjustment.

The invention applies also to styling products such as lacquers, gels, hair setting lotions, mousses, and products for making the hair lank. The content of active agent, for example polymer or sticky or waxy products in general, may be adjusted as a function of the execution of the program, for example as a function of the progress of the treatment.

The invention applies further to products for the durable shaping of the hair, such as perming products or straightening or smoothing products. The content of active agent, for example thiol, alkaline, may be adjusted as a function of the execution of the program, for example of the progress of the treatment.

The invention makes it possible to automatically or semi-automatically optimize the formulation of the product dispensed. The term "automatically" should be understood to mean that the adjustment of the formulation of the product does not require intervention by the user on an adjustment member. The term "semi-automatically" should be understood to mean that the adjustment involves an intervention by the user, that is to say that the user must act manually on an, adjustment member such as for example an adjustment button, a slider or an adjustment thumbwheel, as a function of information provided by the system, for example in a visual manner, for example through an indicator light, a display or a screen, which may or may not be integrated into the system, for example integrated into the packaging and dispensing device, or in an audible manner.

By virtue of the invention, the product which is produced and required to be output with each use of the system by the user may exhibit a concentration, in terms of a primary or secondary active agent, which is optimized for the time of use.

The system can follow the instructions of the program and the adjustment system can adjust the amounts of product dispensed and/or the formulation of the product dispensed, for example by applying a rule for the evolution of the adjustment, stored in the system.

The term primary active agent(s) refers to the active agent(s) giving a product its main efficacy, for example surfactants in the case of a shampoo. The term secondary active agent(s) refers to the active agent(s) playing a role in the embellishment of the product, for example, in the case of a shampoo, the fragrancing active agents or the rheology active agents.

It becomes possible by virtue of the invention to obtain an optimized delivered product, that is to say one which contains the concentration in terms of primary or secondary active agent which is ideal for the time of use. If the system according to the invention is used at some other time, this may require some other adjustment of the concentration of active agent. The invention may serve to adjust the concentration of active agent and/or to vary the nature of the active agent or agents present in the product dispensed, according for example to the number of reservoirs of the packaging and dispensing device and the way in which the adjustment is performed.

In an optional manner, the system is devised to communicate with an expert system. This may make it possible to simplify the system, which may then be devoid of powerful calculation means.

The energy for powering the electronic means and the adjustment system may be supplied by an internal electrical energy source, for example one or more batteries, rechargeable or otherwise, or accumulators, an external electrical energy source, by ambient light or by the user via an energy converter system, for example an electromechanical mechanism actuated by the user.

The energy for dispensing the product and homogenizing it, as appropriate, may be provided by the user via an energy converter or in a direct manner, for example by pressing one or more walls of the packaging and dispensing device. The energy can further be provided by an internal or external electrical energy source, for example by transforming ambient light into electricity by virtue of photovoltaic cells.

The adjustment system may be configured so as to be activated automatically when the user exerts an action on the packaging and dispensing device which is intended to cause the output of the product. For example, the packaging and dispensing device may comprise a switch which is actuated when the user presses on a wall of the device to expel the content of one or more reservoirs towards the outlet or when the user lifts the device or tilts it. This switch may advise the electronic means that a dose has been dispensed and the program can take account thereof. The switch is for example sensitive to pressure and disposed in a zone on which the user bears in order to dispense the product. The switch may further be actuated by the user when the latter presses a button controlling dispensing.

The switch may further be sensitive, and detect for example a modification of the capacitance or conductivity of a predefined zone in the presence of a finger or the hand of the user in the vicinity thereof or in contact therewith.

The cosmetic or dermatological system according to the invention can be configured to modify the concentration of at least one active agent in the product dispensed, in response to the execution of the program.

For this purpose, the packaging and dispensing device can comprise two reservoirs containing two starting compositions, also called starting products, to be mixed so as to form the product delivered, and the adjustment system can make it possible to modify the ratio of one starting product with respect to another during dispensing, as a function of a cue controlling the adjustment system delivered by the electronic means.

The adjustment can for example be performed automatically as a function of the number of uses and/or of the degree of emptying of a reservoir. The degree of emptying of a reservoir may be determined by various means, for example by weighing, calculation of a flow rate and of a duration of dispensing, counting of a number of doses dispensed, measurement of an electrical or optical quantity representative of the amount remaining, among other possibilities. In an exemplary implementation, the system comprises a counter of the number of uses. The higher the number, the greater the provision that may be made for enrichment with active agent and vice-versa, depending on the applications.

The adjustment system and the electronic means for acting on the adjustment system may be integrated into the packaging and dispensing device, being for example contained in one and the same housing as the reservoir or reservoirs, for example in a manner non-separable for the user during the normal use of the device.

The system may be furnished with controllable valves (for example electrovalves, mechanical valves driven by servomotors, etc.), controllable pads (controlled by electromagnet for example), controllable nozzles (inkjet type, etc.), or other servocontrolled means for dispensing or for controlling flow rate, so as to adjust the amounts dispensed.

The system can be configured to execute one or more programs. It can load one or more programs and keep them in memory. The system can be configured to afford the user the possibility of creating, recalling or modifying a program. The system can also afford access to menus of programs, thus allowing the possibility of choosing one of them. Various programs may correspond to as many predefined laws for the evolution of the adjustment as a function of successive uses.

Preferably, the packaging and dispensing device, the electronic means and the adjustment system are integrated into one and the same hand-held apparatus that can be easily manipulated by the user, for example of mass less than or equal to 250 g or preferably less than or equal to 150 g, products excluded.

The system can comprise an interface allowing the user to choose from among several programs governing the evolution of the adjustment or to modify, recall or create a program. The interface can comprise for example a touch screen, one or more buttons or thumbwheels, a keypad, a joystick, a means of voice recognition or a receiver of data originating from a remote control, from a computer or mobile telephone.

The system can be configured to allow the user to identify the program currently executing and/or the degree of progress in the execution of the program. For example, the identifier of the program in progress or the step of the program is displayed on a display, screen, indicator light(s), or is signalled by broadcasting an audible message.

The system can be devised to indicate the state of progress of a treatment to the user.

The system may optionally be devised to also forewarn the user that the amount available of at least one composition is insufficient to finish the treatment.

The system may be configured to receive or load a program, for example emanating from an expert or from a remote transmitter or server or from a similar system. For example, the user can purchase a system comprising the electronic means, without the starting product or products or the program or programs. When purchasing the starting product or products, a suitable program is provided to the user. This program may be standard and the same for all users. The program may also be customized and depend not only on the starting product or products but on the user. The customization may be performed in response to a questionnaire and/or as a function of the result of measurements performed on the user, for example at a point of sale.

A starting product may optionally be packaged in the form of a refill with the corresponding program or parameters governing the evolution of the adjustment. For example, the program or the parameters are recorded on an electronic memory which is read by the apparatus receiving the refill. The memory may be physically bound to the refill.

The system may be furnished with communication means for receiving data, such as means which use the Internet or other networks. It may also receive programs recorded by way of an electronic card reader, for example.

The system may comprise an expert system making it possible to optimize the choice of the program or the execution of the program.

The system according to the invention can send information to an expert or an expert system and receive some back. The information sent by the system allows the expert or the expert system to possibly modify the program selected by the user or certain parameters governing the evolution of the adjustment.

In an exemplary implementation of the invention, the invention makes it possible to optimize a treatment. The program can control the amounts dispensed or the dosages of formulae dispensed, without taking any account of the user's wishes or of personal data in the execution of the program.

The treatment can correspond to a first beginning application and to subsequent applications. For example, the user may wish to dye his or her hair. The treatment corresponds to a beginning application followed by applications which will maintain the dyed look. The program can contain a table advising as to the adjustment to be performed as a function of the number of uses since the first use.

The treatment can also correspond to the applications that the user will carry out although he or she previously used other products. For example, the user already has dyed hair. The treatment corresponds to applications making it possible to maintain the dyed look. For this purpose, the program makes provision, in an exemplary implementation, for the concentration of dye to be variable, decreasing as the applications continue. The programming makes it possible to avoid the effects of unaesthetic overloads.

The treatment can also correspond to the applications that the user will carry out although he or she is using other products in parallel, for example a dyeing treatment. For this purpose, the program can modify the concentration of dye if the person has used a treatment of perming or straightening type. The programming is then designed so that the concentration of dye diminishes less with continuing applications than in the case where the user has not carried out any perming or straightening treatment.

In a general manner, the program may not only modify the formulation of the composition applied and/or the amount dispensed, but also the mode of application.

A change of mode of application may be performed in certain cases automatically, when the device so permits. A change may also be invoked by the system, by signalling to the user the need to replace one application head by another, for example. The application conditions are for example chosen from among application by contact or spraying. Several modes of application by contact may be used and selected as a function for example of the effectiveness sought, for example application by brush, by pad, etc. The mode of application may optionally govern the amount of product dispensed.

The program can also, as a supplement, alter other factors influencing the effectiveness or the dosage of the formula, such as certain conditions of application (duration, temperature, etc.), the conditions of rinsing and/or post-treatment, if any. For example, the system can signal to the user, for example by a visual or audible signal, the end of the contacting of the product with the zone to be treated, the user then having to proceed with rinsing. The duration of contact may vary as a function of the number of uses, being for example smaller and smaller to take account of the rising number of uses. The adjustment does not necessarily vary. The system indicates for example that it retains the same adjustments but that the user must follow a particular exposure time.

The treatment may extend over several months, or over a single day or less. Thus, a treatment may be recommenced each day. Such is the case in particular for makeup, for example for the lips. Two uses of the system are for example separated by more than an hour, a day or a week.

In the case of a daily treatment, the treatment can correspond to a first application, where the amounts are heavily dosed, and then other subsequent applications where the amounts, in lower doses, are intended to maintain an effect, for example makeup, throughout the day. The program can be rerun the next day. The system can comprise a means making it possible to reinitialize it, for example a reinitialization button. As a variant, the reinitialization may be performed automatically, for example as a function of an internal clock or of the receipt of reinitialization data.

The treatment may also relate to the making up of the skin, eyelashes, nails or the holding of the hair in place, the product then being for example a lacquer.

Another benefit of the invention is that it makes it possible to individualize the treatment so as to best match the user's case.

Thus, in an exemplary implementation of the invention, the programming takes account of the user's wishes or of personal factors such as the quality of the skin or hair. The rule for the evolution of the adjustment may thus be customized, and depend on at least one parameter external to the system, for example a parameter characteristic of the user, of a sought-after result and/or of an environment of the user. The system can comprise in memory several laws for the evolution of the adjustment as a function of the value of at least one parameter of the user or of the environment of the user. The selection of the evolution law can be automatic by the system, once the parameter or parameters have been advised.

In numerous cases, the opinion of an expert may improve the fit between the person's desires and the result. Indeed, the expert can analyse the factors which point to the choice of one product rather than another or one application procedure rather than another.

In this case, two approaches are possible. The person can visit the expert for each application. For example, the person visits their beautician or hairdresser. This approach is fairly expensive and requires considerable time to be devoted to their treatment.

The person can thus follow the advice of the expert and carry out the applications themselves. This approach may become complicated, if only because it is not always easy to follow a prescription.

In exemplary embodiments of the invention, an expert intervenes to identify a program of application of the product.

The expert then programs the system or provides the user with information allowing the user to program the system or to load the suitable system.

Subsequently, it is still possible to call on the expert to optimize the program.

It is also possible to involve an expert system. It may be based on forms to be filled in, photographs or diagrams, so as to carry out or transmit the program that the system according to the invention will follow.

The invention also makes it possible to optimize an evolution, for example so as to colour the skin or optimize the aesthetics of transition from noncoloured skin to coloured skin or optimize the aesthetics of transition from coloured skin to noncoloured skin or optimize the aesthetics of transition from one colour to another.

The invention may also be applied to the treatment of wrinkles, to the dyeing of the hair and of the skin and to perming and straightening treatments. The invention can make it possible to have a more discreet and/or more aesthetic evolution.

Many people experience difficulties when buying their cosmetic product, for example because they have not yet chosen the result that they desire or have not yet identified the personal factors which steer them to buy one product rather than another. Care products for greasy skin are available in several strength versions. If the user does not know how to classify their skin, the user will not know which strength to purchase and may hesitate in purchasing the product. By virtue of the invention, the person can purchase the product without hesitation, and then, at home, select the program governing the evolution of the adjustment as a function of their skin so that the product has the best possible efficacy.

Though the program makes it possible to optimize the use of the product, the invention also allows the user to discover possibilities that they do not necessarily suspect. Thus, the system can broadcast information explaining the possibilities of the product.

The system can make it possible to refill the packaging and dispensing device with one or more products.

The subject of the invention is also a method of cosmetic treatment of human keratinic matter, especially the skin, lips or hair, in which a cosmetic product is applied to said matter, this product being dispensed by a system comprising a packaging and dispensing device comprising at least one starting composition, an adjustment system making it possible to vary a property of the product dispensed and/or the amount dispensed, in which method the adjustment system is controlled automatically by an electronic means executing a program, the evolution of the adjustment being performed as a function at least of a quantity representative of the number of uses of said device and/or of the amount of the product dispensed and/or of the amount of one at least of the starting compositions which is dispensed, or in which an adjustment cue is emitted to the user so that he or she acts on the adjustment system.

The adjustment can be modified as a function at least of the number of uses of the packaging and dispensing device.

The adjustment can be modified as a function at least of the level of composition in a reservoir of the packaging and dispensing device.

The adjustment can be modified as a function at least of the product amount already dispensed.

According to exemplary embodiments, the electronic means is configured to detect the use of the packaging and dispensing device, and the adjustment is performed at least as a function of the number of uses thus detected.

The electronic means can comprise a switch sensitive to the actuation of a dispensing means.

The electronic means can be configured to detect the level of composition in at least one reservoir of the packaging and dispensing device and the adjustment can be performed at least as a function of the level in this reservoir.

The system can comprise a base stand associated with the packaging and dispensing device, comprising the electronic means, the base stand being configured to control the adjustment system.

The system can comprise a plurality of packaging and dispensing devices, associated with one and the same base stand.

Program

The prime purpose of the program may be to control the dispensing and/or dosing of the formulae dispensed, so as to comply with a predefined law of evolution suited to the treatment to be carried out.

It may, moreover, give instructions that will have to be followed by the user, for example regarding the exposure time, regarding the technique for applying or rinsing the product, etc.

A program may comprise a set of instructions, executable in series and/or in parallel. The instructions may relate directly to the dispensing of one of the starting products, for example the flowing of this product from a reservoir to a dispensing orifice for a given time.

The instructions may comprise a set of actions for dispensing products, for example flow of a first starting product, then flow of a second starting product, and so on and so forth, or flow of a starting product in a first amount, and then flow of the same starting product in a second amount and so on and so forth.

The instructions may relate to numerical or logical calculations, required for optimizing the dispensing of one or more products. For example, the program can take account not only of a number of uses but also of the lag between the various uses, to calculate the amounts dispensed at each use and/or the concentrations of active agents.

The program can be stored by mechanical means (perforated card, etc.), optical means (bar codes) or by electronic or electromagnetic means (memory cards or hard or optical disk). This storage may be definitive, or temporary.

The system can be devised to make it possible to select a program. This selection can be left to the assessment of the user or of the expert, if any, assisting the user. For this purpose, the system can propose a menu of the various programs, with elements helping selection, for example a quotation of the program as a function of the hoped-for result or a simulation of the result.

For example, in the case of an antiacne treatment, the system can propose several programs, mentioning the characteristics of the program (for example number of applications per day) and the expected results (for example disappearance of spots in x days).

The system can also take charge of choosing the program without leaving the choice of the program to the user.

The system can be furnished with means helping the user to select a program.

The system can make it possible to load or download the program, for example from a website. The program can be initially recorded on a memory card to be inserted into a reader of the system.

The memory card can be associated with means of identification and/or authentication aimed at avoiding the reproduction of the program by an unauthorized person.

The system can be furnished with means enabling it to be advised either as to program that the user wishes to use, or as to data which will help the system to choose the program. The system can be devised to obtain data required for the execution of a selected program. For example, the program can submit a questionnaire to the user after at least one step of the treatment, so as to ascertain the result of this step, and determine a possible modification of the adjustment following the result observed.

As mentioned above, the system can comprise an interface, comprising for example an information input means, for example chosen from among touch screens, keypads, mice, thumbwheels, buttons, pads, joysticks, voice controls, etc., the communication systems able to gather data or programs (for example radio transmission, WIFI, Bluetooth, local electrical network).

The system can further comprise one or more sensors making it possible to better ascertain the characteristics of the user and/or the result of a treatment, for example a skin colour sensor or a texture sensor or one or more sensors making it possible to ascertain exterior characteristics, for example a sensor of humidity, light (incorporating all or some of the visible, UVB, UVA, IR spectrum), temperature, electrical conductivity, magnetic and electric field, pressure and/or altitude, wind, precipitations, fog, ionization, liquid or solid particles, transparency of the air, a gaseous chemical compound ($CO_2$, CO, $N_2$, $O_2$, $O_3$, $NO_2$, $NO_3$), a particular atom (for example sulphur).

The system can be designed so as to be advised as regards exterior elements, for example the signalling or a forecast of pollution, a weather forecast, etc.

The evolution of the adjustment may thus be made as a function not only of the progress in the treatment but of conditions specific to the user and/or to their environment.

In an exemplary embodiment of the invention, the execution of the program can be interrupted, either to reset it to zero, or to change it, or to switch to a manual mode where the program no longer controls the dispensing and/or dosing of the product. In this case, the system can store the actions that the user has carried out since the interruption, with a view to taking account thereof in the case of switching to automatic mode again.

The actions carried out may be analysed in such a way as, if required, to incorporate them into the calculations when resuming the execution of the program or to propose one or more programs taking account thereof to the user.

Multireservoir System

The system can be furnished with at least two reservoirs.

The flow rate of at least one of them can be supervised, in an exemplary implementation of the invention.

The reservoirs can comprise respectively a neutral fluid and a fluid enriched with active agent.

To alter the properties of the product dispensed, it is possible to vary the diameter of an outlet channel, or to displace a shutter in the outlet channel so as to limit the passage of the fluid. This can be undertaken by a component which can move in translation, in rotation, propelled by a motor, by a magnetic field or an electric field.

The system can be furnished with more than two reservoirs. The system can act for example on several feed channels to enrich the mixture with one or more active agents.

Energy-Activated System

An energy may be used to activate a deactivated active agent.

For this purpose, an amount of fluid is conveyed to the outlet. Before the outlet, the system sends the energy to activate the deactivated active agent. Only the active agent present in the amount of fluid exposed to the energy is activated. The active agent remaining in the body of the reservoir remains deactivated. This makes it possible to modify the potency of the product on each use.

Configurations

The system according to the invention can comprise a base stand associated with the packaging and dispensing device, comprising for example the electronic means. The base stand can comprise a control means for acting on the adjustment system as a function of information originating from the electronic means.

The base stand may or may not be secured to the packaging and dispensing device during the use of the latter to dispense the product. The base stand may be mounted in a removable manner on the packaging and dispensing device.

The system can comprise a plurality of packaging and dispensing devices associated with one and the same base stand. The user can for example couple the base stand to the packaging and dispensing device containing the starting product or products on the basis of which the product must be dispensed. As a variant, the base stand operates the packaging and dispensing device remotely in the course of use. As another variant, the packaging and dispensing device having to be used is temporarily coupled up to the base stand for adjustment requirements, and then separated from it when dispensing the product.

The system can take account of internal information, relating for example to the level of one or more reservoirs, or to a measurement of flow rate of a product dispensed from a reservoir.

The system can constitute a hand-held assembly. The system can also comprise, as appropriate, the packaging and dispensing device in the form of a hand-held piece and a base stand. The packaging and dispensing device is for example devised to be positioned on the base stand in the absence of product dispensing. The base stand can be devised to weigh the packaging and dispensing device, this possibly making it possible to ascertain the amount dispensed and to modify the adjustment, so as for example to change the concentration of an active agent.

The base stand can comprise a part at least of the adjustment system. For example, the base stand can comprise an actuator able to act on a member for adjusting the device when the latter is placed on the base stand or coupled in some other manner to the base stand. The packaging and dispensing device can comprise the reservoirs containing the starting products and a product dispensing means. When the user separates the packaging and dispensing device from the base stand, the adjustment is that which was defined by the base stand. The latter can serve, as appropriate, as a docking station for a mobile telephone, which can control the adjustment system.

The invention may be better understood on reading the detailed description which follows, of nonlimiting exemplary implementations thereof, and on examining the appended drawing, in which:

FIGS. 1 to 7, 10, 14, 15, 17 to 19 represent, schematically, exemplary systems according to the invention, and FIGS. 8, 9, 11 to 13, 16 and 20 represent in a schematic and partial manner exemplary adjustment systems.

Represented in FIG. 1 is an exemplary cosmetic or dermatological system 10 according to the invention, comprising one or more reservoirs 11 containing one or more compositions on the basis of which a product is dispensed, these compositions also being called starting products. The system 10 comprises an adjustment system 12 and an electronic means 13 allowing the execution of a program governing the evolution of the properties and/or of the amount of the product dispensed.

As illustrated in this example, the adjustment system 12 can be controlled at least by an item of information originating from the electronic means 13, so as to adjust the concentration of active agent(s) in the product dispensed and/or the amount dispensed.

Figure 2:
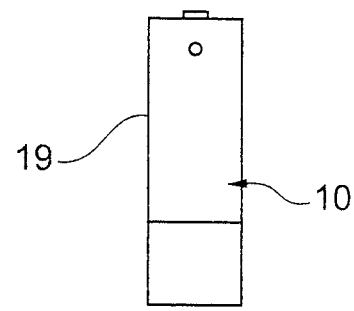

The system 10 can comprise a packaging and dispensing device comprising for example a housing which contains the starting product or products, the adjustment system 12 and the electronic means 13 making it possible to act on the adjustment system within the framework of the execution of the program, as illustrated in FIG. 2.

Figure 3:
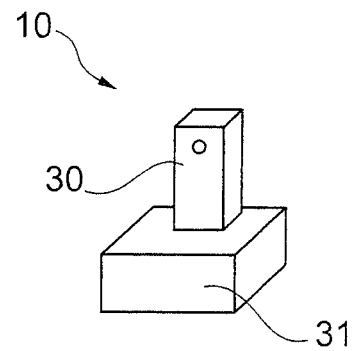

As a variant, as illustrated in FIG. 3, the system 10 comprises a packaging and dispensing device 30 which can be separated from a base stand 31, which comprises for example all or part of the adjustment system and electronic means for acting on the adjustment system.

In this case, the packaging and dispensing device comprises for example the starting products and a means of dispensing a mixture formed from the starting products. A member for adjusting the device can be actuated by the base stand as a function of the content of active agent in the product to be dispensed.

The reservoir or reservoirs of the system according to the invention can be rechargeable or not, being separable or not from the packaging and dispensing device. The packaging and dispensing device can allow a change of one or more reservoirs by the user, as appropriate.

In a variant, the system allows a change of the electronic means and/or of the adjustment system.

Figure 4:
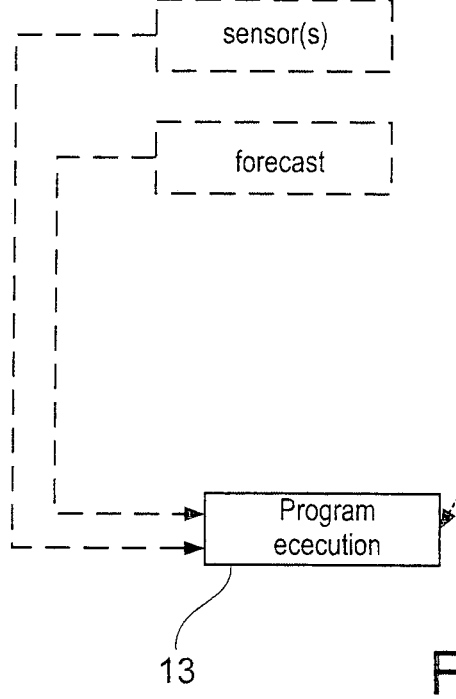
Figure 4:
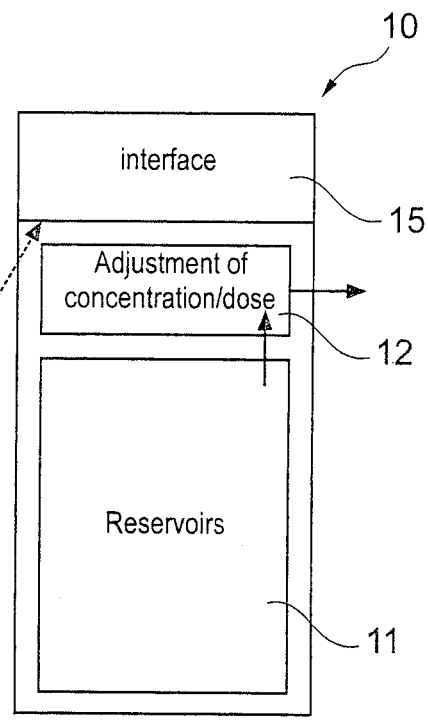

The packaging and dispensing device can itself be furnished with an interface 15 for capturing the information from the electronic means 13, with the help of waves or wire, as illustrated in FIG. 4.

Figure 5:
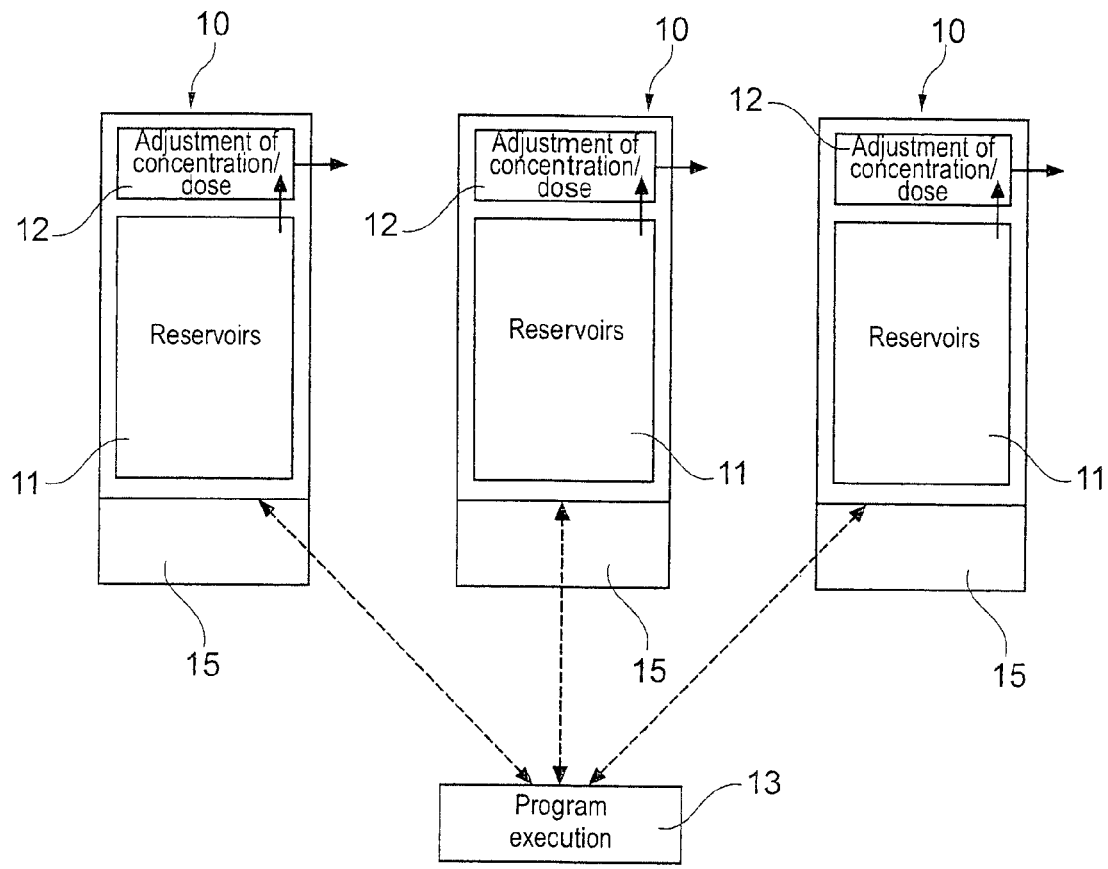

In the particular case illustrated in FIG. 5, the electronic means 13 is common to several packaging and dispensing devices.

For example, a bathroom is furnished with a base stand comprising the electronic means in interaction with several packaging and dispensing devices. In this case, the packaging devices each comprise a local interface 15 for receiving the data transmitted by the electronic means 13.

The expert system or systems may be integrated or not into the packaging and dispensing device.

Figures 6, 7:
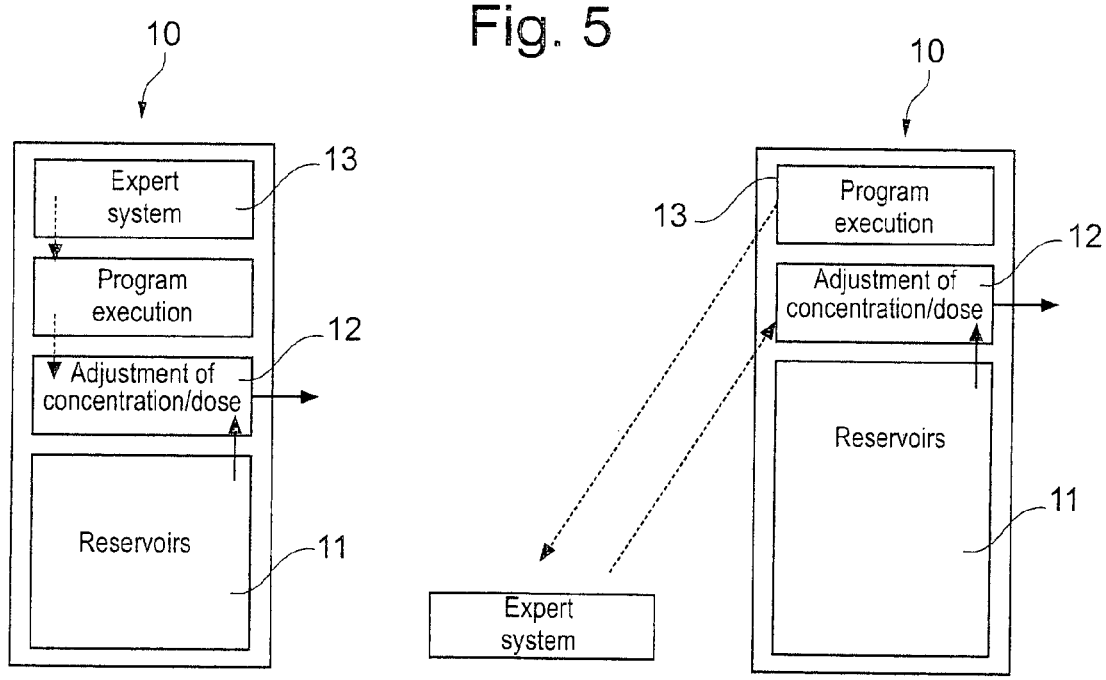

The system according to the invention can exchange data with an internal or external expert system, as illustrated respectively in FIGS. 6 and 7.

In the case where the system is adapted to be used by several people, the system can also identify the user and keep in memory the program to which it should refer depending on the user. For example, the system can comprise a selector making it possible to indicate who the user is. As a variant, the system is capable of automatically recognizing the user, for example through biometric information.

In so far as several packaging and dispensing devices can be cosited in the same location, and that these devices are not used in the same way, provision may be made for the signal sent by the electronic means to be able to be identified by the adjustment system associated with each packaging and dispensing device, in such a way as to ensure that it does indeed correspond thereto. Thus the electronic means can send an identification code in the signal, and the adjustment system can be furnished with a comparison system for identifying the code corresponding to it. In this way, the adjustment system follows instructions which are addressed to it and not the instructions intended for another packaging and dispensing device.

A packaging and dispensing device can also be devised to inform the electronic means that it is present and/or that it is turned on. It can also inform of the compositions available to it, and the electronic means can exploit same so as to best adapt the instructions.

In a particular case of the invention, an electronic means, one or more treatment means and one or more adjustment systems are brought together. The system is designed to dispense several different products, for example in the form of interchangeable reservoirs, or in the form of products placed on a mobile dispensing rack.

With such a system, the electronic means can adjust all the packaging and dispensing devices.

In a particular case of the invention, the system is devised to allow the user to forego the adjustment, which is no longer carried out automatically as a function of the execution of the program and which is carried out according to other modes of operation, including manual, for example.

Manner of Dispensing and Adjustment System

The system can comprise one or more packaging and dispensing devices. Each device can comprise several reservoirs whose contents, for example liquids, are mixed in variable proportions, as a function of the execution of the program and, as appropriate, of additional information, this additional information being delivered for example by one or more ambiance sensors or being transmitted by a data transmitter external to the system.

The system can comprise a packaging and dispensing device comprising several different starting products and the adjustment system can be devised to make it possible to selectively dispense one of the starting products as a function of the execution of the program.

The device can comprise two reservoirs and the adjustment system can act by modifying the flow rate of the product originating from one at least of the reservoirs.

One of the reservoirs of the device can contain a neutral starting product and the other reservoir a starting product enriched with active agent, whose concentration it is sought to vary in the product delivered, as a function of the running of the program. The flow rate of the product enriched with active agent may be adjusted by the system according to the invention before mixing with the neutral product, in such a way as to have the desired concentration of active agent in the mixture.

Figure 8:
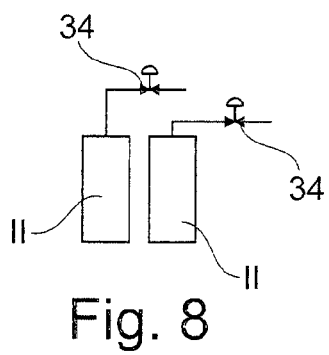

To vary the flow rate, it is possible to alter the flow section offered to the product leaving the reservoir or reservoirs 11, by virtue of one or more valves 34, as illustrated in FIG. 8. For example, it is possible to use a pinch valve which acts by squeezing a flexible duct to a greater or lesser extent, or a needle valve which acts by displacing a needle in a fluid flow channel. This displacement may be ensured by a movable component of the adjustment system, this component being for example displaced in translation or in rotation or according to a more complex motion, being for example propelled by a motor, by a magnetic field or an electric field.

Figure 9:
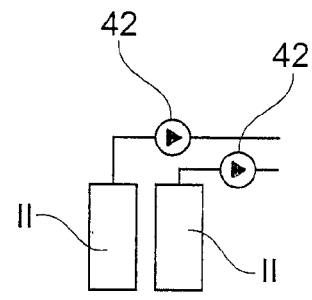

It is furthermore possible to act on the flow rate of a pump 42 so as to vary the content of an active agent in the dispensed product, as illustrated in FIG. 9, said pump 42 serving for example to extract the active agent in the corresponding reservoir.

The system according to the invention can comprise more than two reservoirs and the adjustment system can adjust the flow rate of all or some of the products originating from these reservoirs so as to enrich the mixture with one or more active agents.

In a variant implementation of the invention, the device is configured to carry out a volumetric dosing by allowing through a given volume of each of the starting products, either successively, or simultaneously, to the outside or into a mixing chamber.

In certain exemplary implementations of the invention, an energy will activate an initially deactivated active agent, contained in a starting product, as a function of the running of the program.

The adjustment system can act for example in all or nothing mode on the activation of the active agent or in a gradual manner.

Figure 10:
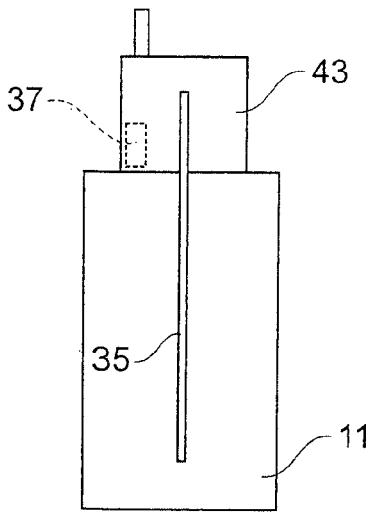

The activation of the active agent may be done while dispensing the product, by passing the active agent into an activation chamber 43, as illustrated in FIG. 10. The activation of the active agent can be done on a predefined amount of the product, fixed or variable, before the dispensing thereof by the device.

For example, a certain amount of product contained in a reservoir of the device is conveyed into the activation chamber 43. Before exit, the device sends the energy to activate the deactivated active agent. Only the active agent present in the activation chamber is activated. The active agent remaining in the reservoir remains deactivated.

On each use, the degree of activation of the active agent may be different, as a function of the running of the program.

To cause the starting product to enter the activation chamber, it is possible to use a device such as that represented in FIG. 10, comprising one or more flexible walls which the user can press to cause the product to rise from a reservoir 11 into the activation chamber 43, for example by way of a dip tube 35. An activation device 37 is present in said chamber. The product, after activation, can be extracted from the activation chamber 43 by any means, for example by pumping, overpressure generated by the user in the activation chamber, pouring or extraction by means of an applicator.

The active agent can be activated by the effect of an energy such as heat or light.

In the case where several starting products are mixed, the device can be furnished with at least one mixing chamber allowing the active agent to be homogenized before it leaves the device.

The mixing can be done on exit from the device. The device can comprise a member for agitating the mixture before the dispensing thereof, for example a ball. The device can furthermore comprise a dispensing tip comprising baffles.

When the device comprises two reservoirs containing starting products to be mixed extemporaneously, mixing can take place outside the device.

Figure 11:
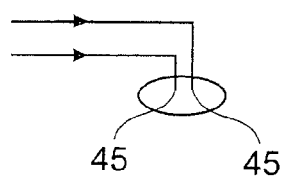

For example, the starting products to be mixed emerge on the outside through distinct dispensing orifices 45, as illustrated in FIG. 11. These orifices are advantageously close together, so as to allow the user to easily extract the amounts dispensed. The starting products can contact one another outside the device, on a surface where the extraction takes place.

In certain exemplary embodiments, the device comprises two reservoirs with flexible walls, each reservoir, being furnished with a discharge channel. These may emerge in proximity to one another, for example at a distance of less than or equal to 5 mm from one another.

Several possibilities exist for allowing the dispensing of a product with the desired contents of active agents.

For example, the dispensing device can comprise two reservoirs containing different starting products, the first reservoir comprising for example a neutral product and the second reservoir an active agent. The term "neutral product" should be understood to mean a product intended to be mixed with at least one product containing a primary or secondary active agent so as to produce the product to be dispensed.

The proportion of active agent in the product delivered can be adjusted by modifying the head loss in ducts linking the reservoirs containing the starting products and the corresponding dispensing orifice or orifices.

Figure 12:
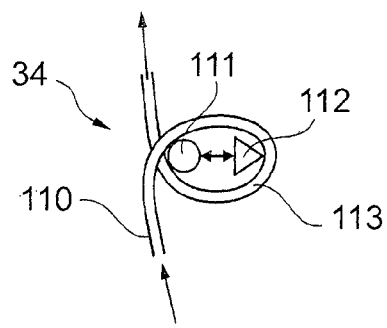

Provision may for example be made, as illustrated in FIG. 12, for a device for pinching a duct 110 in which one of the starting products flows. For example, this duct 110 describes a loop while bearing on a support 111 of the device and a movable separating element 112 controlled by the system can separate from the support 111 to a greater or lesser extent so as to squeeze the duct 110 to a greater or lesser extent. The separating of the movable element 112 is for example controlled by a motor. The element 112 is for example of triangular shape and a spring can pull it against the duct 110 in the absence of power supply to the motor. When the motor is powered, the element 112 is displaced towards the support 110 and the duct re-assumes a larger internal cross section through elasticity. The motor used is for example a stepper motor, for example of Performax type, and the duct is for example a flexible plastic tube 3 mm in diameter.

Adjustment of the proportions of the various starting products can furthermore be obtained by ensuring a greater or lesser actuation stroke for pumps actuated by the user to dispense the product and respectively associated with the various starting products. For example, the pumps may comprise push-in control stems and one of the stems may be actuated over a constant stroke to dispense the neutral product while the other stem is actuated with a variable stroke to dispense the active agent which is mixed with the neutral product, this variable stroke being obtained, for example, by virtue of a transmission element controlled by a motor.

The products may furthermore be dispensed by displacing pistons over a greater or lesser stroke.

Figure 14:
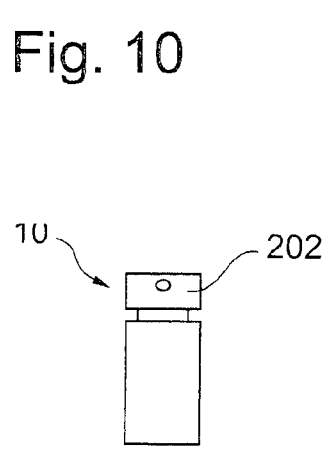

In FIG. 14 is represented a device which has a screen 170 on which an adjustment recommendation may be displayed.

The packaging and dispensing device can comprise a manual adjustment member 201 making it possible to adjust the concentration of active agent in the product which is dispensed. In this case, the device operates in a semi-automatic manner. The user actuates the adjustment system as a function of the advice displayed. As appropriate, the screen 170 may form part of a base stand detachable from the packaging and dispensing device comprising the reservoirs, so as to allow the use of the base stand with other products.

Figure 13:
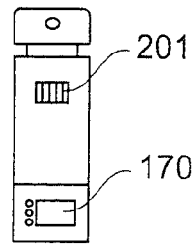

In FIG. 13 is represented a system 10 comprising a dispensing head 202 which can be actuated by the user to dispense the product.

Figure 15:
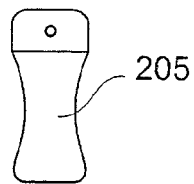

The dispensing of the product may be performed furthermore, as illustrated in FIG. 15, by furnishing the dispensing device with a body having a deformable wall 205, which makes it possible for example to reduce the interior volume of the reservoir or reservoirs containing the starting product or products.

Figure 16:
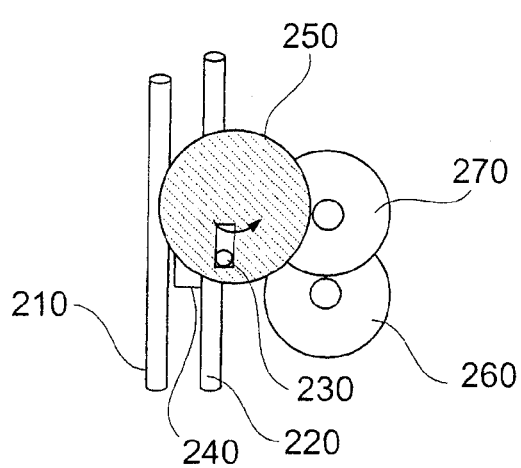

In the example of FIG. 16, the device comprises two reservoirs containing the starting products, linked to two outlet ducts 210 and 220, for example two flexible tubes made of plastic 3 mm in diameter.

One 210 of the ducts may be permanently open and the other 220 obturated with a variable degree of obturation by a pinch valve, comprising for example a piano wire 230, for example a piano wire 1 mm in section and 3 cm long. The wire is positioned in a prestressed manner so as to squeeze the duct onto a fixed rigid component 240 of the device, which supports for example moreover the other duct 210. The natural elasticity of the piano wire 230 is sufficient to pinch the duct 220 at rest and to prevent the passage of the product, even when the user presses the corresponding reservoir.

The other end of the piano wire 230 may be engaged in a small toothed wheel 250 furnished with a slot. This wheel is driven by a DC motor 260 and a gear train 270 increasing the torque from the motor, proportional to the current.

When the motor 26D is powered, it transmits its torque to the wheel 250, which pulls on the piano wire 230 and separates it from the fixed component 240. The bigger the current delivered to the motor 260, the less the piano wire squeezes the duct 220 and the more it allows the product the possibility of passing if the user presses the second reservoir. When the motor is no longer powered, the elasticity of the piano wire 230 returns it again to bear against the duct 220, which is squeezed against the fixed component 240.

The energy required for the starting products to exit may be ensured in this example by the user, by pressing the two flexible reservoirs. Thus, no liquid exits the reservoirs and can pass through the outlet ducts if the user does not press on the reservoirs.

Figure 17:
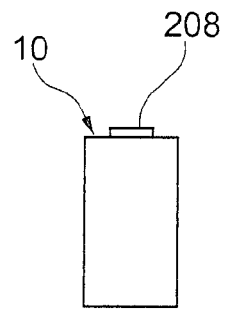

In FIG. 17 is illustrated the possibility of the device not comprising any means of actuation by the user to provide the energy required for dispensing. For example, the device can comprise a trigger button 208 which the user can press to trigger the automatic dispensing of the product, by virtue of the activation of a pump for example.

Figure 18:
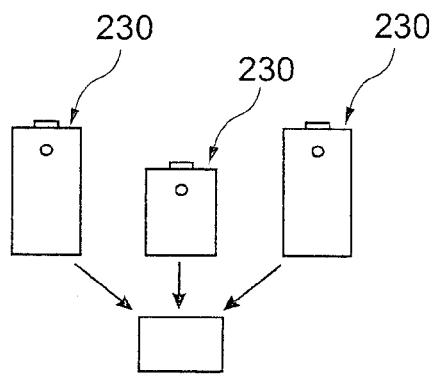

As appropriate, as illustrated in FIG. 18, several packaging and dispensing devices 230 may be associated with one and the same base stand 220.

The base stand 220 is advantageously devised so as to automatically recognize the product or products contained in the device 230 which is coupled thereto, so as to take account thereof in the adjustment performed. This recognition is performed for example by virtue of electrical contacts, an electronic chip, for example RFID, a mechanical feeler and/or an optical reader.

As appropriate, the base stand serves as docking station for a mobile telephone of the Iphone® or other kind, which may serve as user interface, serve as electronic means and perform all or some of the calculations for converting data into control instructions for the adjustment system.

The packaging and dispensing device may, as appropriate, be devoid of any electrical adjustment actuator. The latter may be present only on the base stand, and cooperate through a mechanical transmission with an adjustment member present on the hand-held component, for example a flow rate adjustment valve.

Figure 19:
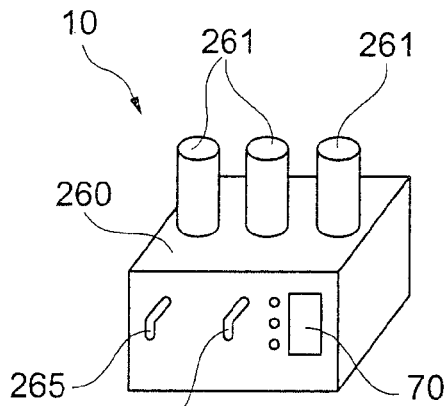

The system according to the invention is not necessarily miniaturized to the point of being able to be held in the hand and may for example take the form, as illustrated in FIG. 19, of a more bulky apparatus, for example intended to be placed on a display counter or on a shelf in a bathroom. Such a system may comprise a housing 260 to which may be fixed in a removable manner receptacles 61 containing the various starting products that can be mixed, as well as one or more ducts 265 for dispensing one or more products whose properties are suited to the conditions of use by virtue of the execution of the program.

EXAMPLES PROPOSED

A system furnished with two flexible reservoirs Ra and Rb is produced, each reservoir being furnished with a discharge channel, the two emerging for example 4 mm apart. Thus, when the two products contained in the reservoirs are discharged, the user recovers a mixture formed by contact and rapid diffusion of the two products.

Figure 20:
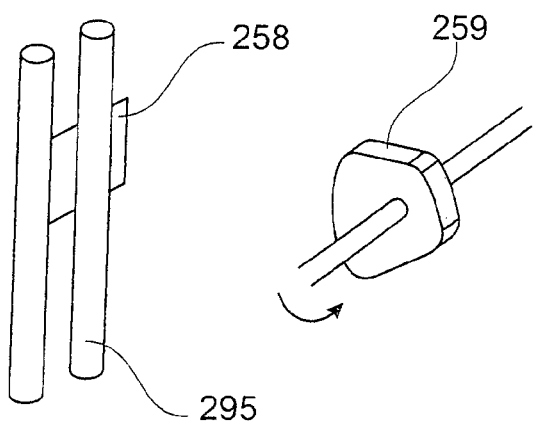

The outlet channel of the first reservoir is for example a flexible plastic tube 3 mm in diameter and 25 mm long and the outlet channel of the second reservoir is for example a flexible plastic tube 3 mm in diameter and 25 mm long, held by a rigid and fixed component 258 on the rear face, as illustrated in FIG. 20. A cam 259 is placed in front of the outlet channel 295 of the second reservoir. In the rest position, the cam compresses the channel. When the spindle of the cam rotates, the cam frees the duct from its compression.

The energy required for the liquids to exit is ensured by the pressure that the user inputs by pressing the two flexible reservoirs. Thus, no liquid exits the reservoirs and passes through the channels if the user does not press on the reservoirs.

A switch is placed on the first reservoir. When the user grasps the packaging and dispensing device in their hand, they press on the reservoir and close the switch. When the user is not holding the device, the switch is open.

A logical network of CPLD type, with the brand name Altera, of Max II type, may be used as electronic means.

This type of logical network is miniature, preprogrammable and energy frugal and can be powered continuously by an integrated 3 V battery.

One of the inputs/outputs of the logical network is connected to the switch and another of the inputs/outputs of the logical network is connected to a servomotor.

The programming of the logical network provides for:

The incrementation of a value I each time the switch is closed.

The comparison of the value I with a conversion table S. The output of the table S gives the degree of enrichment of the corresponding fluid in the final mixture.

The translation of the output data S of the conversion table into a PWM signal, for controlling the servomotor.

This corresponds to the activation of the servomotor, hence to the rotation of the cam, and hence the degree of opening of the channel of the second reservoir.

As long as the switch is closed, the PWM signal is maintained. If the switch is released, the cancellation of the PWM signal is not carried out until a minute after release.

The system is hooked up to a memory containing the conversion table.

The servomotor is capable of carrying out ½ of a revolution according to the PWM signal. The servomotor is also connected to the electrical power supply (5 V).

A cap covers the top of the system to prevent the ingress of dirt.

Example 1

Product for Treating the Skin

The first reservoir Ra is filled with a gel containing 20% of glycerine and the second reservoir Rb with a gel containing 30% of UV filter.

Two programs are provided. The first corresponds to a treatment program for delicate skin and the second to a treatment program for normal skin.

Conversion table for the "delicate skin" program

| I | S |
|---|---|
| 1 | 10 |
| 2 | 10 |
| 3 | 9 |
| 4 | 9 |
| 5 | 8 |
| 6 | 8 |
| 7 | 7 |
| 8 and above | 6 |

Conversion table for the "normal skin" program

| I | S |
|---|---|
| 1 | 10 |
| 2 | 9 |
| 3 | 8 |
| 4 | 6 |
| 5 | 5 |
| 6 | 4 |
| 7 | 3 |
| 8 and above | 2 |

The user removes the cap and actuates the switch by seizing the device. They use the product once a day. After a few seconds, they press the flask, forcing the two liquids to discharge through the respective channels.

The system ensures, after each use, protection of the skin suited to the type of skin.

Example 2

Skin Colouring Product

The first reservoir Ra is filled with a neutral gel and the second reservoir Rb with a gel containing DHA.

The program makes it possible to colour the skin and maintain it over time. On each use, the system calculates and delivers an optimal product. The device is used every four days.

Conversion table

| I | S |
|---|---|
| 1 | 10 |
| 2 | 6 |
| 3 | 4 |
| 4 and above | 3 |

The user removes the cap and actuates the switch by seizing the device.

After a few seconds, they press the flask, forcing the two liquids to discharge through the respective channels. Depending on the time, the mixture is more or less enriched with DHA.

After a first application making it possible to achieve a tanning effect, the subsequent applications maintain, without excess, the colour of the skin.

The invention is not limited to the examples described.

The expression "comprising a" should be understood as being synonymous with "comprising at least one".

The invention claimed is:

1. Cosmetic or dermatological system, comprising:
a packaging and dispensing device comprising one or more compositions on the basis of which a product is delivered,
an adjustment system coupled or able to be coupled to the packaging and dispensing device, making it possible to modify the amount dispensed and/or at least one property of the product dispensed by the packaging and dispensing device,
an electronic means for executing a program and acting automatically on the adjustment system, or for indicating to the user an action to be exerted on the adjustment system, so as to make the adjustment evolve in the course of the use of the device, the program determining the evolution of the adjustment as a function at least of a quantity representative of the number of uses of said device or of the amount of said product or of at least one of said compositions and already dispensed, the electronic means being configured to detect the use of the packaging and dispensing device, and the adjustment being performed at least as a function of the number of uses thus detected, the electronic means comprising a switch sensitive to the actuation of a dispensing means for dispensing the product, wherein the dispensing means dispenses the product with energy provided directly by the user.

2. System according to claim 1, the said quantity corresponding to the number of uses of the device.

3. System according to claim 1, being configured to modify the concentration of at least one active agent in the product dispensed as a function of the adjustment.

4. System according to claim 1, the packaging and dispensing device comprising two reservoirs containing two starting products to be mixed to form the product delivered, the adjustment system making it possible to modify the ratio of one starting product with respect to the other, during dispensing.

5. System according to claim 1, the packaging and dispensing device comprising two reservoirs containing two different starting compositions, the adjustment system being configured to selectively dispense one of the starting compositions.

6. System according to claim 1, the adjustment system comprising an energy source for exposing at least one composition contained in the packaging and dispensing device to a stimulus, this composition comprising at least one active agent that can pass from an inactive state to an active state upon exposure to said stimulus.

7. System according to claim 1, comprising a base stand associated with the packaging and dispensing device, comprising the electronic means, the base stand being configured to control the adjustment system.

8. System according to claim 7, comprising a plurality of packaging and dispensing devices, associated with one and the same base stand.

* * * * *